(12) United States Patent
Yau et al.

(10) Patent No.: US 8,135,492 B2
(45) Date of Patent: Mar. 13, 2012

(54) METHOD OF MAKING A SURGICAL TEMPLATE USED FOR A COMPUTER-GUIDED DENTAL IMPLANT SURGERY

(75) Inventors: Hong-Tzong Yau, Minsyong Township (TW); Chuan-Chu Kuo, Jhongpu Township (TW); Jiun-Ren Chen, Shueilin Township (TW); Chun-Chun Yang, Dali (TW); Chien-An Chen, Lujhu Township (TW); Ying-Li Chen, Kaohsiung (TW)

(73) Assignee: Pou Yu Biotechnology Co., Ltd., Changhua Hsien (TW)

( * ) Notice: Subject to any disclaimer, the term of this patent is extended or adjusted under 35 U.S.C. 154(b) by 217 days.

(21) Appl. No.: 12/713,849

(22) Filed: Feb. 26, 2010

(65) Prior Publication Data

US 2010/0240000 A1     Sep. 23, 2010

(30) Foreign Application Priority Data

Mar. 19, 2009   (TW) ................................ 98108925 A

(51) Int. Cl.
*G06F 19/00* (2011.01)
*A61C 9/00* (2006.01)
*A61C 13/08* (2006.01)

(52) U.S. Cl. .......... 700/182; 700/98; 700/117; 700/164; 700/197; 433/37; 433/44; 264/19; 264/101; 264/219

(58) Field of Classification Search ............ 700/98, 700/117, 160, 161, 163, 164, 182, 197, 198, 700/205; 433/37, 44, 48; 264/16, 19, 39, 264/101, 219; 703/1

See application file for complete search history.

(56) References Cited

U.S. PATENT DOCUMENTS

2010/0009308 A1*   1/2010   Wen et al. ...................... 433/24
2011/0129792 A1*   6/2011   Berckmans et al. ............ 433/72

* cited by examiner

*Primary Examiner* — Sean Shechtman
(74) *Attorney, Agent, or Firm* — Schwabe, Williamson & Wyatt P.C.

(57) ABSTRACT

A method of making a surgical template used for a computer-guided dental implant surgery includes the steps of: establishing implant planning data of a patient's jaw, producing a digital plaster model of the patient's jaw, allowing the digital plaster model to have the implant planning data, integrating the digital plaster model with the implant planning data to obtain a digital machining data, holding and machining a modeling block at a machining position according to the digital machining data to form a solid jaw model corresponding to the patient's jaw and having teeth, gums, and at least one implant-position indicating structure, mounting a positioning member at the implant-position indicating structure, and producing a negative template body from an assembly of the solid jaw model and the positioning member with a thermoplastic dental material by a molding process or a vacuum forming process.

22 Claims, 18 Drawing Sheets

METHOD OF MAKING A SURGICAL TEMPLATE USED FOR A COMPUTER-GUIDED DENTAL IMPLANT SURGERY

CROSS-REFERENCE TO RELATED APPLICATION

This application claims priority of Taiwanese Application No. 098108925, filed on Mar. 19, 2009.

BACKGROUND OF THE INVENTION

1. Field of the Invention

This invention relates to a dental surgical template, and more particularly to a method of making a surgical template used for a computer-guided dental implant surgery.

2. Description of the Related Art

A conventional method of making a surgical template used for a computer-guided dental implant surgery disclosed in Taiwanese Patent No. 093121438 is shown in FIGS. 1 and 2. In step 101, silicone is applied within a casing 14, and is pressed against a patient's jaw. After the silicone is cured, it forms a negative surgical template body 11.

In step 102, in an imaging process, a three-dimensional geometrical image of the patient's jaw is obtained by computerized tomography (CT) technique. Subsequently, the three-dimensional geometrical image is provided to a computer for analysis to thereby further obtain implant planning data, such as depth, length, position, inclination angle, etc.

In step 103, a movable support is moved to adjust the position and inclination angle of the negative template body 11 such that the negative plate body 11 can be drilled to form implant guide holes 12 according to the data obtained in the step 102.

In step 104, a plurality of sleeves 13 are inserted respectively into the implant guide holes 12 in the negative template body 11 to thereby form the surgical template for guiding a drill through the negative template body 11 and into the patient's jaw during dental implant surgery.

In the conventional method, to apply the implant planning data to the negative template body 11 for performing the hole-drilling step and the sleeve-inserting step, it is necessary to relate the negative template body 11 with the computer-operated virtual three-dimensional geometrical image of the patient's jaw. However, in such correlation, since only a small amount of overlapping portions occur between the negative template body 11 and the virtual three-dimensional geometrical image, it is difficult to correct the distortions in CT scan of the patient's jaw. As a result, several repeated corrections are required to obtain a comparatively accurate surgical template 11, which reduces the efficiency of the conventional method.

SUMMARY OF THE INVENTION

The object of this invention is to provide a method of making a surgical template used for a computer-guided dental implant surgery, which can apply accurately, precisely, and efficiently virtual implant planning data to the surgical template.

According to an aspect of this invention, a method for making a surgical template used for a computer-guided dental implant surgery comprises the steps of:

(a) producing a three-dimensional model by a CT scanning performed on a patient's jaw and establishing corresponding implant planning data to obtain a digital model of an assembly of the patient's jaw and the implant planning data;

(b) making a negative model by direct impression modeling of the patient's jaw, and then a positive plaster model from the negative model, and producing a digital plaster model corresponding to the positive plaster model;

(c) positioning the digital model of the assembly of the patient's jaw and the implant planning data relative to the digital plaster model to allow the digital plaster model to have the implant planning data;

(d) integrating the digital plaster model with the implant planning data to obtain a digital machining data;

(e) holding and machining a modeling block at a machining position by a machine according to the digital machining data to form a solid jaw model corresponding to the patient's jaw and having teeth, gums, and at least one implant-position indicating structure;

(f) mounting a positioning member at the implant-position indicating structure; and (g) producing a negative template body from an assembly of the solid jaw model and the positioning member with a thermoplastic dental material by one of a molding process and a vacuum forming process such that the negative template body has a lower surface complementary to the assembly of the solid jaw model and the positioning member, and at least one guide hole formed therethrough at a position corresponding to the implant-position indicating structure;

whereby, the surgical template includes the negative template body.

Since the digital plaster model is a positive model, the implant planning data can be applied accurately, precisely, and efficiently to the digital plaster model, thereby allowing the implant guide holes to be formed at ideal positions. Hence, time required for correcting the distortions in CT scan of the patient's jaw can be reduced significantly, thereby promoting the efficiency of the method of this invention and reducing the manufacturing costs of the surgical template.

According to another aspect of this invention, a method of making a surgical template used for a computer-guided dental implant surgery comprises the steps of:

(a) producing a three-dimensional model by a CT scanning performed on a patient's jaw and establishing corresponding implant planning data to obtain a digital model of an assembly of the patient's jaw and the implant planning data;

(b) making a negative model by direct impression modeling of the patient's jaw, and then a positive plaster model from the negative model, and producing a digital plaster model corresponding to the positive plaster model;

(c) positioning the digital model of the assembly of the patient's jaw and the implant planning data relative to the digital plaster model to allow the digital plaster model to have the implant planning data;

(d) integrating the digital plaster model with the implant planning data to obtain a digital machining data, the digital machining data including a plaster model and at least one implant-position indicating unit configured as a pin extending from the plaster model;

(e) holding and machining a modeling block at a machining position by a machine according to the digital machining data to form a solid jaw model corresponding to the patient's jaw and having teeth, gums, and at least one implant-position indicating structure configured as a pin extending from the solid jaw model; and (f) producing a negative template body from the solid jaw model with a thermoplastic dental material by one of a molding process and a vacuum forming process such that the negative template body has a lower surface complementary to the solid jaw model, and at least one guide hole formed therethrough at a position corresponding to the implant-position indicating structure;

whereby, the surgical template includes the negative template body.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Figure 1:
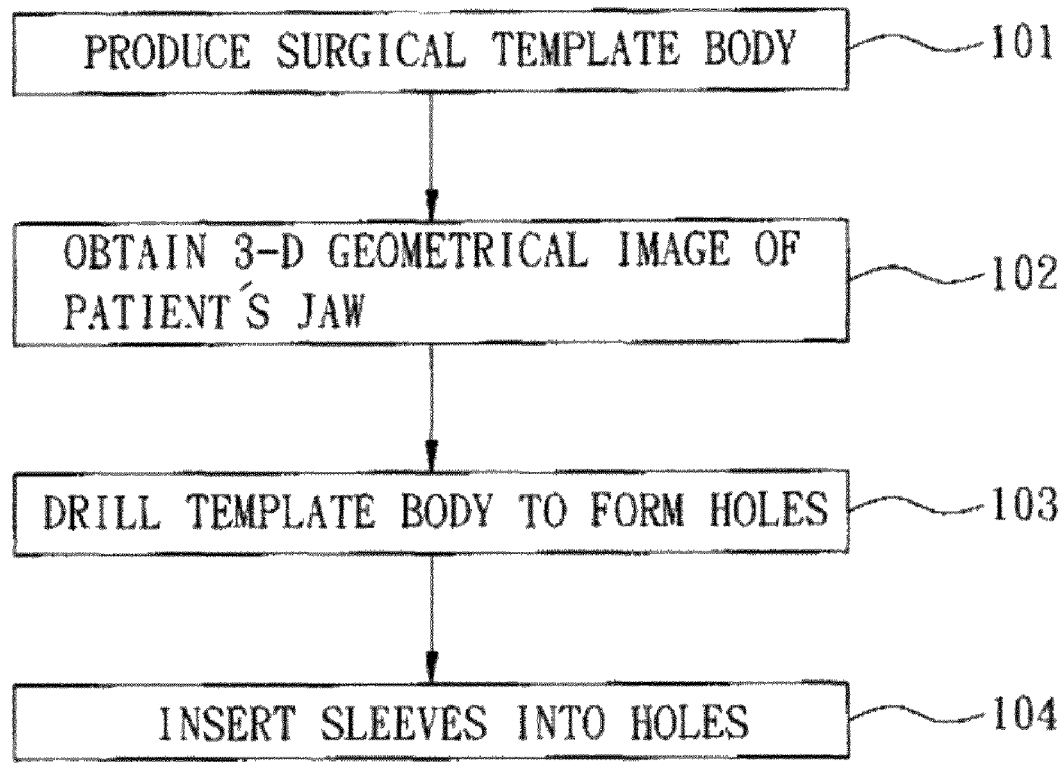
FIG. 1 is a flowchart of a conventional method of making a surgical template for dental implant disclosed in Taiwanese Patent No. 093121438.
Figure 2:
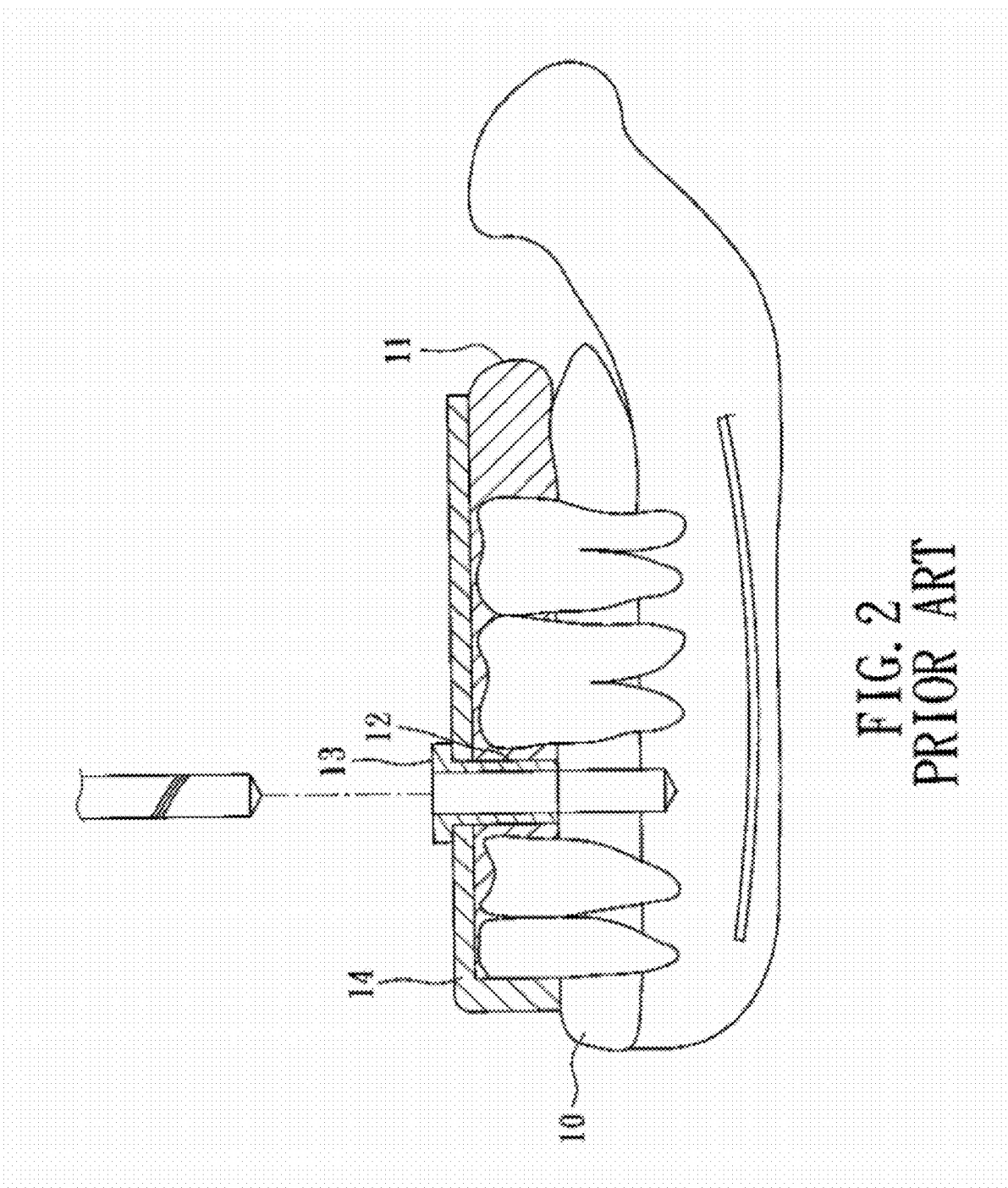
FIG. 2 is a partly sectional view illustrating how a negative template body is formed in the step 101 of the conventional method.

Before the present invention is described in greater detail in connection with the preferred embodiments, it should be noted that similar elements and structures are designated by like reference numerals throughout the entire disclosure.

Figure 3:
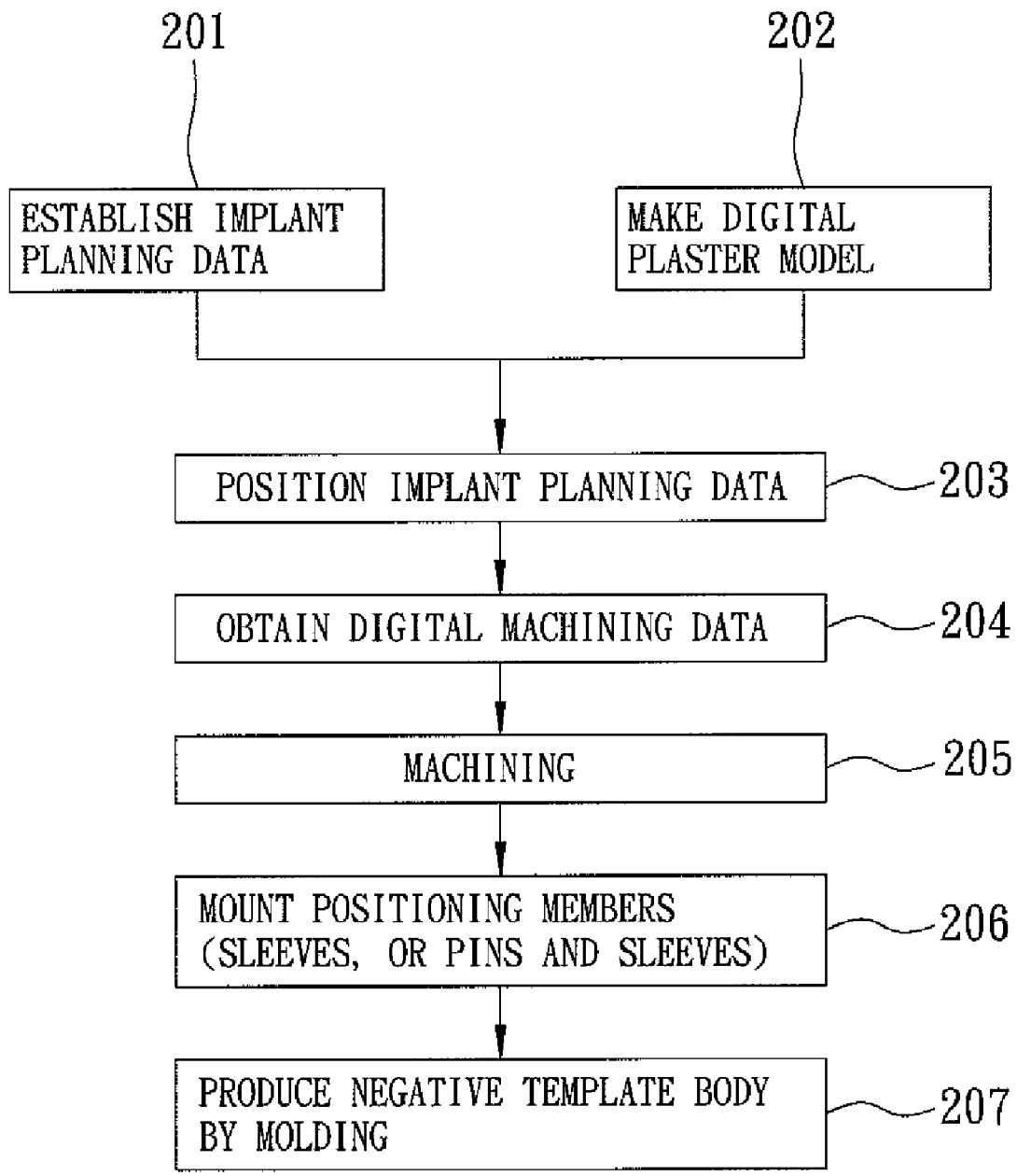
FIG. 3 is a flowchart of the first preferred embodiment of a method of making a surgical template used for dental implant surgery according to this invention.

FIG. 3 is a flowchart illustrating the first preferred embodiment of a method of making a surgical template used for dental implant surgery according to this invention.

Figure 4:
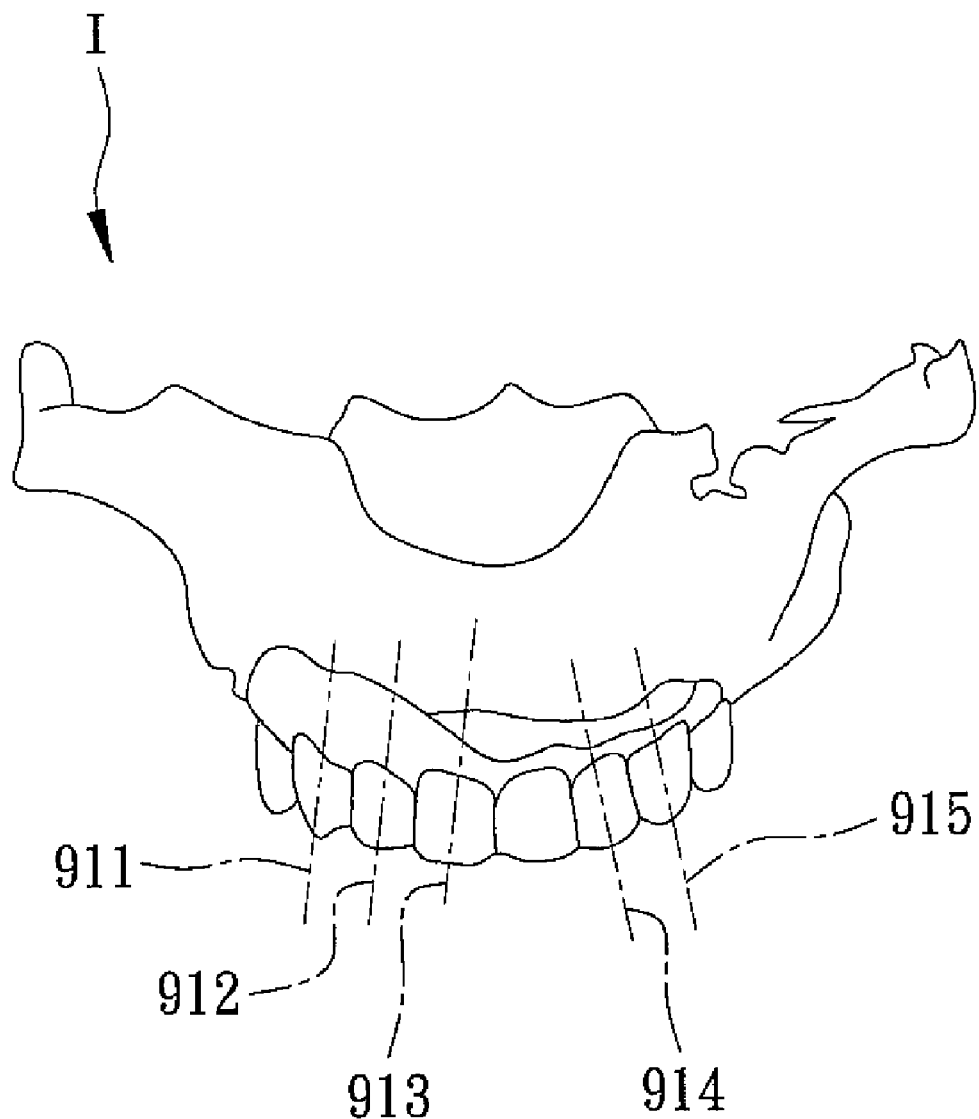
FIG. 4 is a three-dimensional digital image of an assembly of a patient's jaw and implant planning data.

In step 201, a three-dimensional model is produced by a CT (computerized tomography) scanning performed on a patient's jaw. The three-dimensional model is provided to a computer for analysis to thereby establish implant planning data, such as depth, length, position, and inclination angle, based on teeth axes 911-915 (see FIG. 4). Hence, a digital model (I) (see FIG. 4) of an assembly of the patient's jaw and the implant planning data is obtained.

Figure 5:
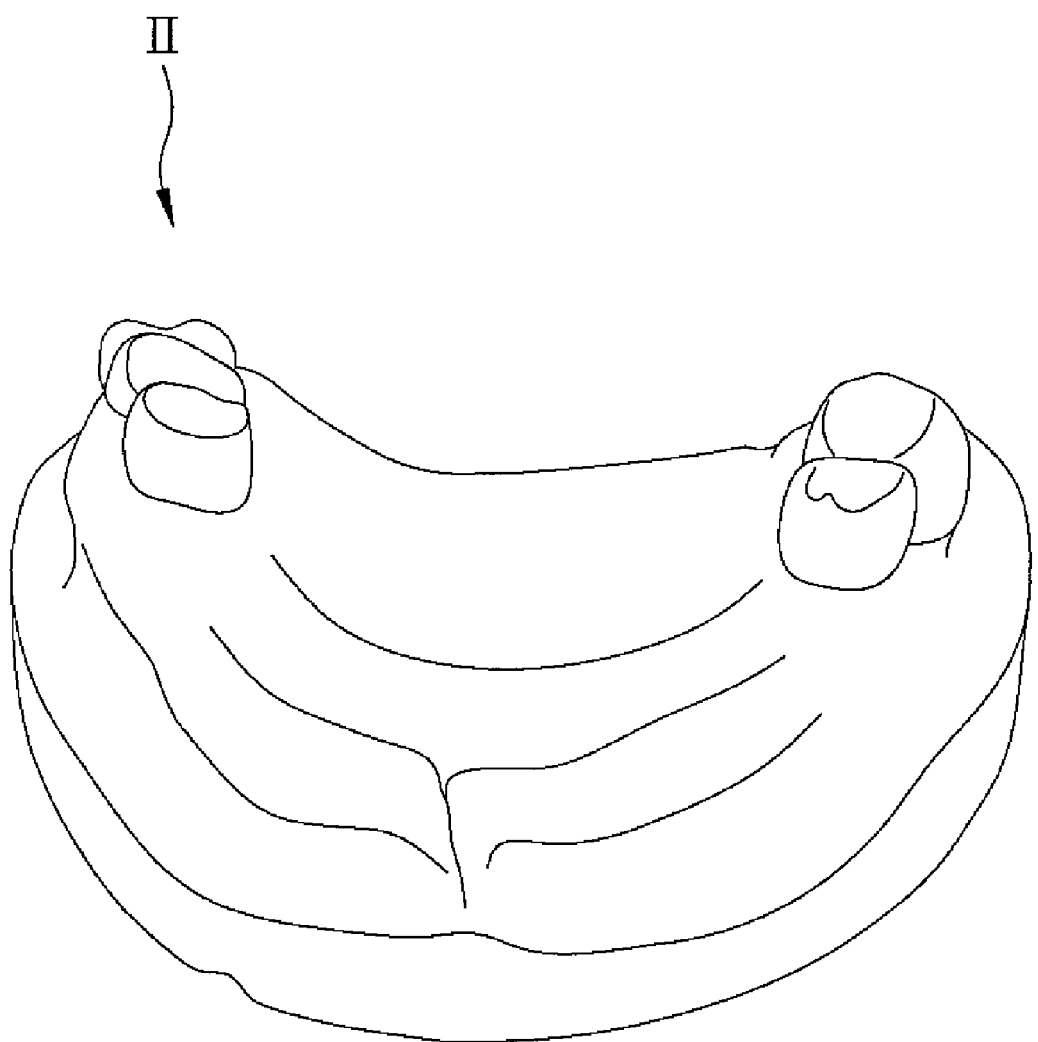
FIG. 5 is a schematic perspective view of a positive plaster model of the patient's jaw to be scanned to form a digital plaster model.

In step 202, a negative silicone model (not shown) is made by direct impression modeling of the patient's jaw. Then, a positive plaster model (II) (see FIG. 5) is made from the negative silicone model. The positive plaster model (II) is scanned to form a digital plaster model (III) (see FIG. 6).

Figure 6:
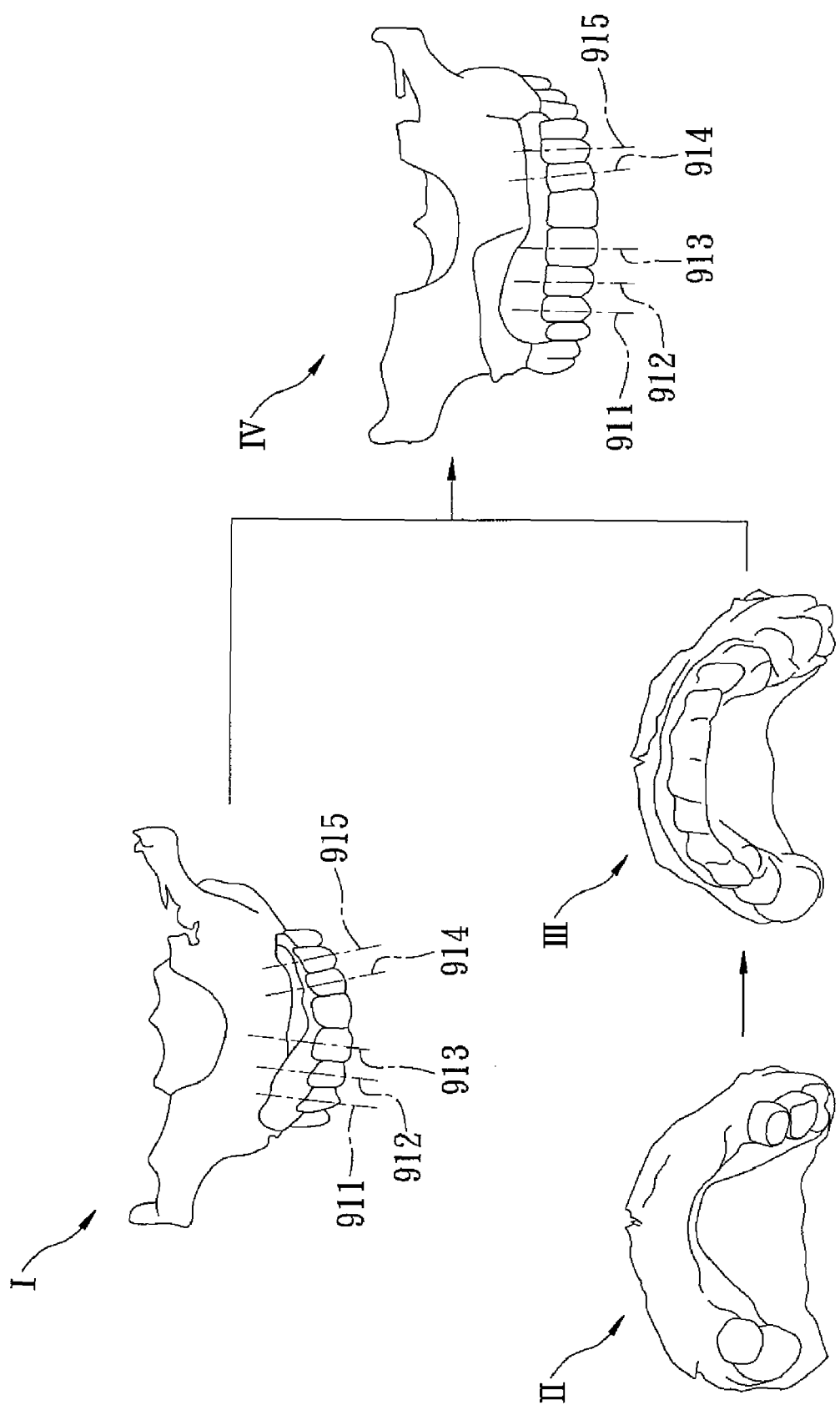
FIG. 6 is a schematic view illustrating how to allow the digital plaster model to have the implant planning data.

Referring to FIG. 6, in step 203, the digital plaster model (III) is positioned relative to the digital model (I) to allow the digital plaster model (III) to have the implant planning data.

In step 204, the digital plaster model (III) is integrated with the implant planning data to obtain a digital machining data (IV) including a plaster model and a plurality of implant-position indicating units. Each of the implant-position indicating units is configured as one of a pinhole formed in the plaster model of the machining data, and a pin extending from the plaster model of the machining data. In this embodiment, each of the implant-position indicating units is configured as the pin extending from the plaster model of the machining data.

Figure 7:
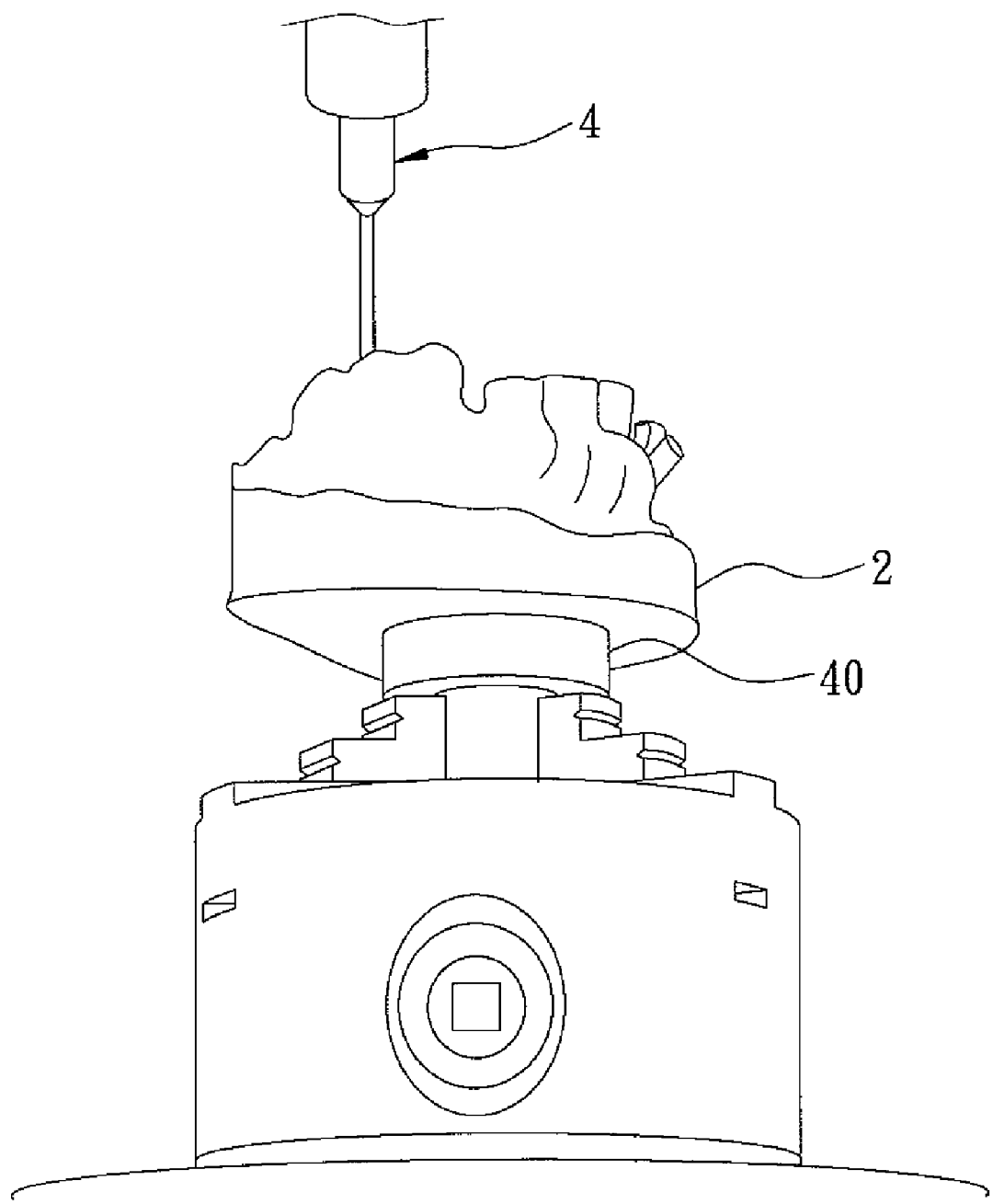
FIG. 7 is a schematic view of a modeling block and a machine.

In step 205, with further reference to FIG. 7, a modeling block 2 is held on a machine bed 40 of a CNC machine 4. Then, with further reference to FIG. 8, the modeling block 2 is machined according to the digital machining data (IV) to form a solid jaw model 3 corresponding to the patient's jaw and having teeth 31, gums 32, and a plurality of implant-position indicating structures 33. Since each of the implant-position indicating units in the step 204 is configured as the pin extending from the plaster model of the machining data, each of the implant-position indicating structures 33 is configured as a pin extending from the solid jaw model 3. In this embodiment, the CNC machine is a five-axis CNC machine, and the modeling block 2 is made of one of plaster and a substitute wood material.

In step 206, a plurality of positioning members 5 are mounted respectively at the implant-position indicating structures 33. Each of the positioning members 5 is configured as a sleeve.

Figure 9:
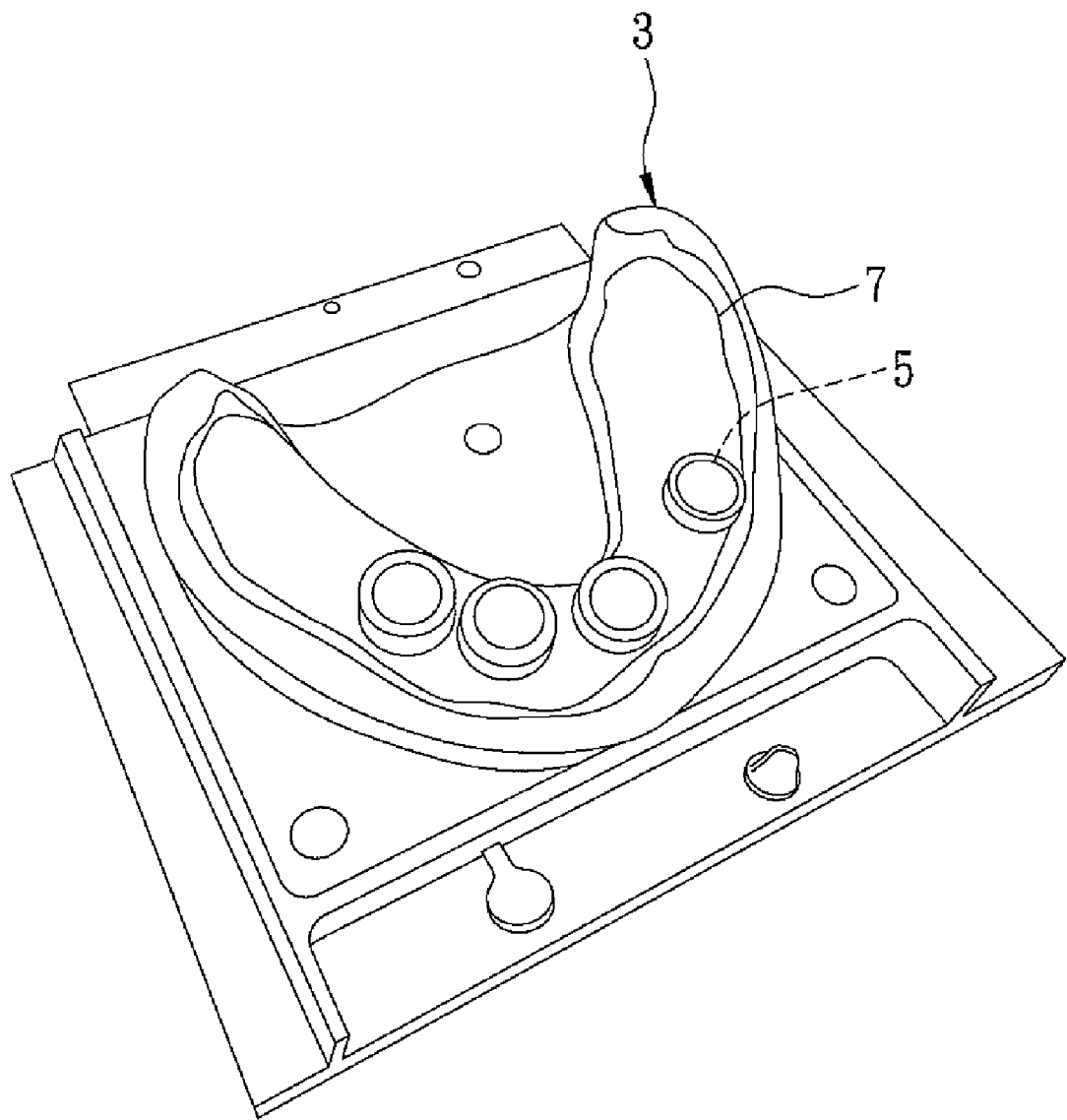
FIG. 9 is a schematic perspective view illustrating a first coating material coated on the solid jaw model and a plurality of positioning members each configured as a sleeve.
Figure 10:
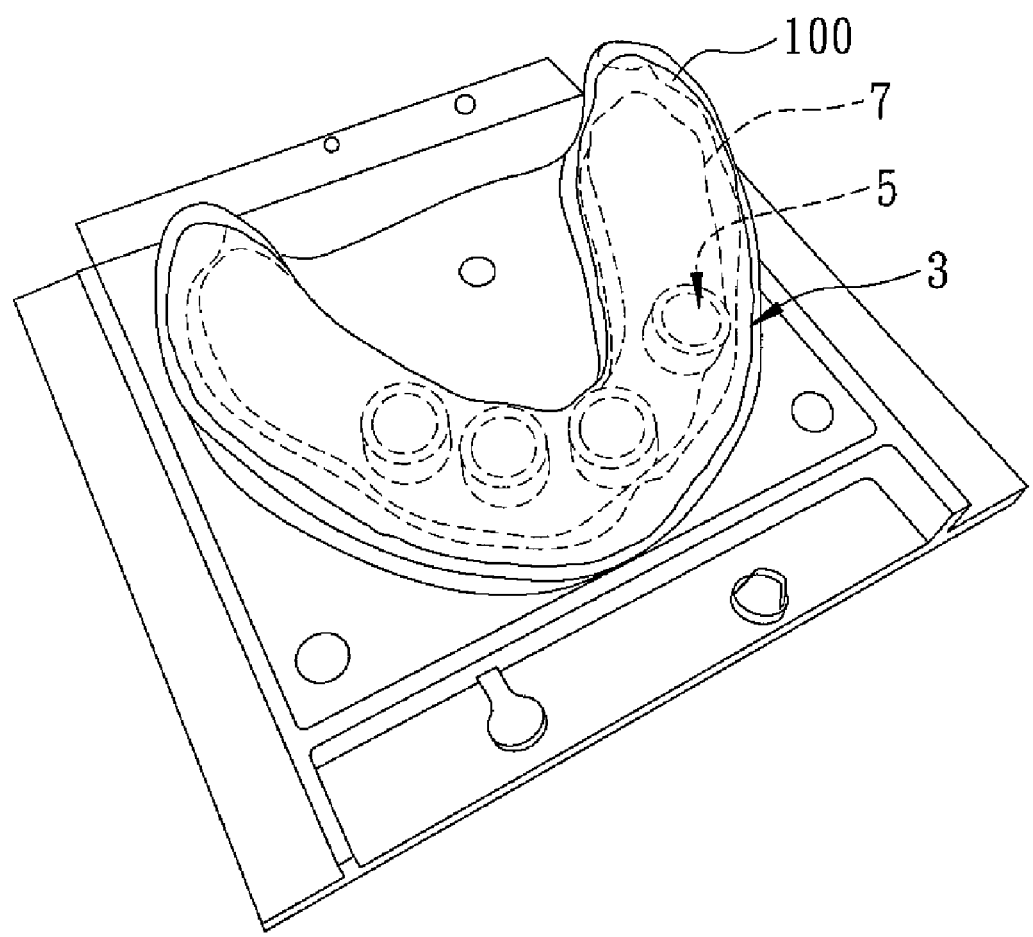
FIG. 10 is a schematic perspective view illustrating a second coating material coated on the first coating material.
Figure 11:
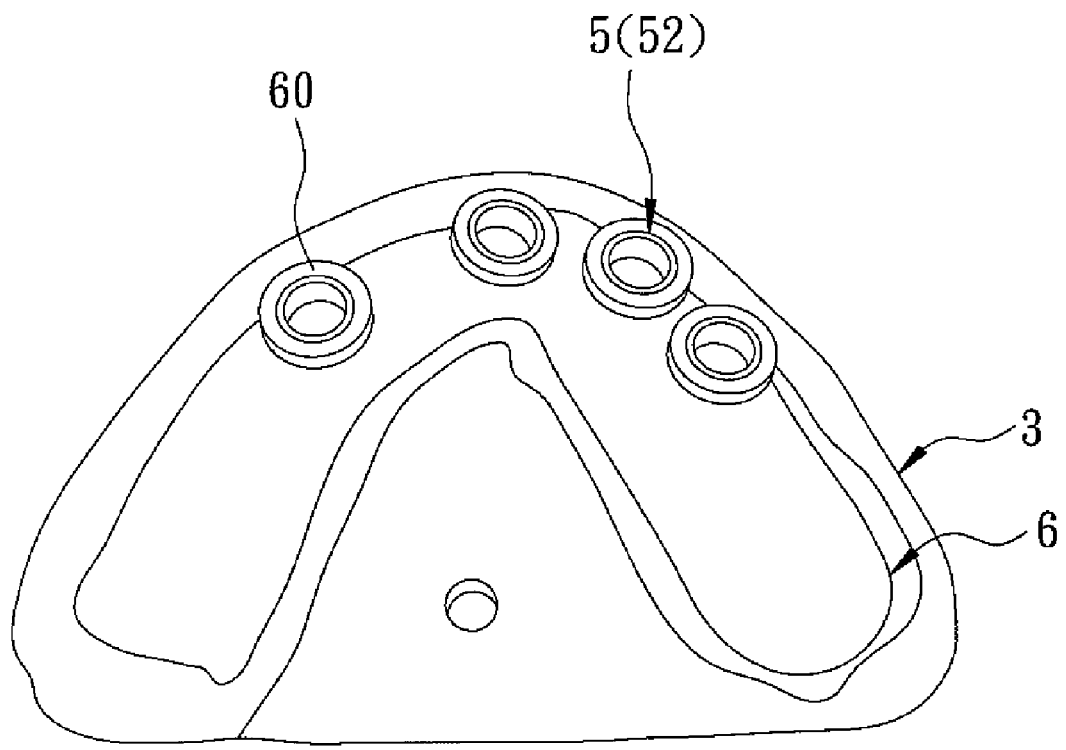
FIG. 11 is a schematic view of the surgical template made by the first preferred embodiment, which includes a negative template body and the positioning members.

With further reference to FIGS. 9, 10, and 11, in step 207, a negative template body 6 is produced from an assembly of the solid jaw model 3 and the positioning members 5 with a thermoplastic dental material by a molding process. The negative template body 6 has a lower surface complementary to the assembly of the solid jaw model 3 and the positioning members 5, and a plurality of implant guide holes 60 formed therethrough at positions corresponding to the implant-position indicating structures 33, respectively.

The molding process includes the following steps:

(1) Referring to FIG. 9, a thermoplastic first coating material 7 is coated on the assembly of the solid jaw model 3 and the positioning members 5. The first coating material 7 has an outer surface 71 that is aligned with end surfaces of the positioning members 5. In this embodiment, the first coating material 7 is wax.

(2) Referring to FIG. 10, a second coating material 100 is coated on the first coating material 7. The second coating material 100 has a melting point higher than that of the first coating material 7. In this embodiment, the second coating material 100 is silicone.

(3) The first and second coating materials 7, 100 are heated to a temperature between the melting points of the first and second coating materials 7, 100 so as to melt only the first melting material 7, thereby forming a mold cavity having the same shape as the negative template body 6. As such, the solid jaw model 3, the positioning members 5, and the second coating material 100 constitute cooperatively a mold.

(4) The dental material is heated and poured into the mold cavity.

(5) When cured, the dental material forms the negative template body 6.

(6) The second coating material 100, the positioning members 5, and the solid jaw model 3 are removed from the negative template body 6.

(7) The negative template body 6 is ground and polished.

Figure 8:
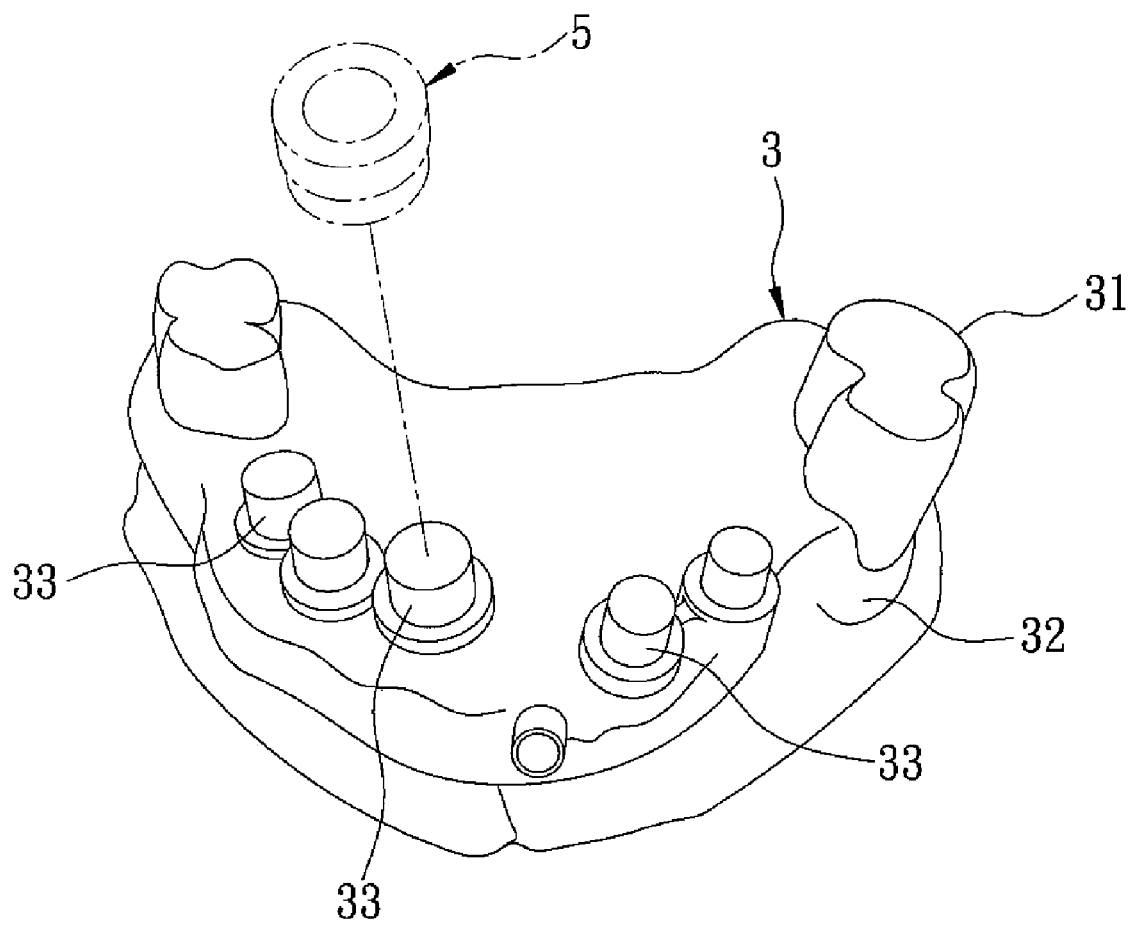
FIG. 8 is a perspective view of a solid jaw model formed from the modeling block by the machine.
Figure 12:
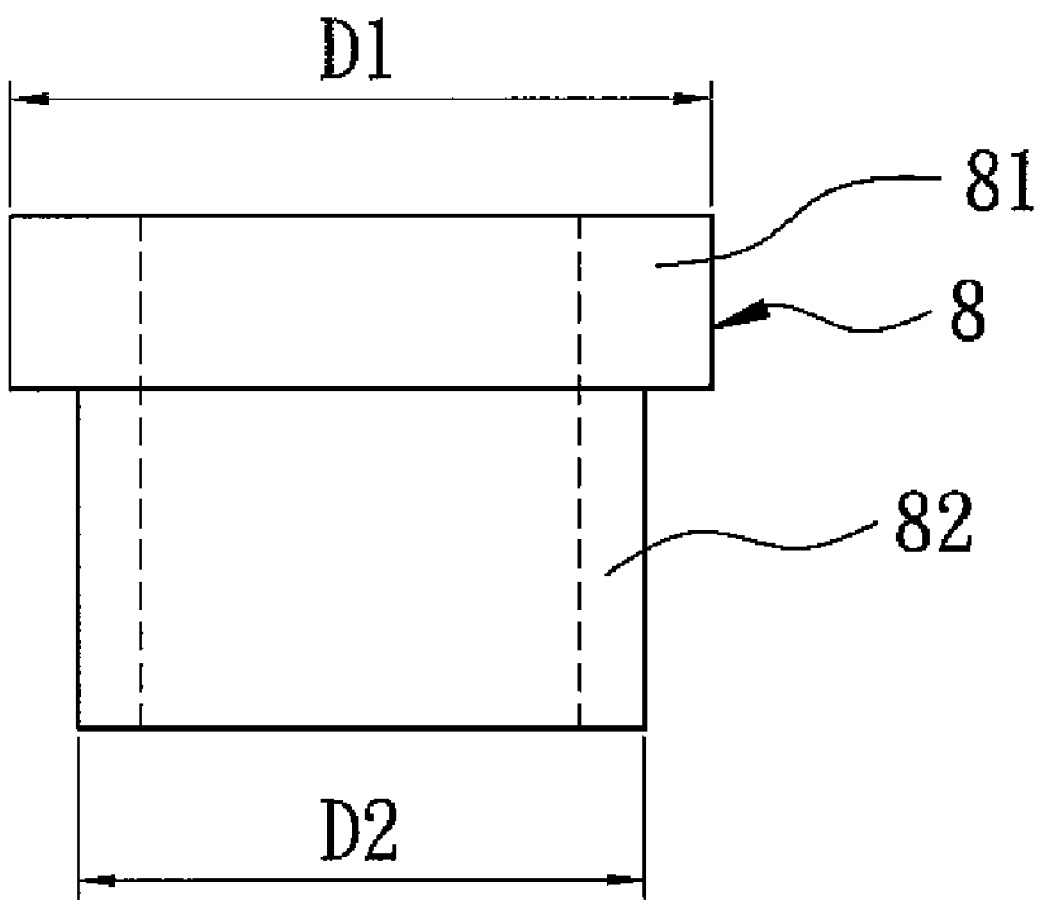
FIG. 12 is a schematic side view of one of the positioning members of FIG. 11.

With reference to FIGS. 8 and 12, since each of the implant-position indicating structures 33 is configured as the pin, as described above, each of the positioning members 5 is configured as a sleeve that is sleeved on the corresponding implant-position indicating structure 33. As such, in this embodiment, the surgical template includes the negative template body 6 and the positioning members 5, as shown in FIG. 11. The sleeves are made of metal. The size of the implant-position indicating structures 33 is set by dentists, and the inner diameter of the sleeves is equal to the outer diameter of the implant-position indicating structures 33.

Figure 13:
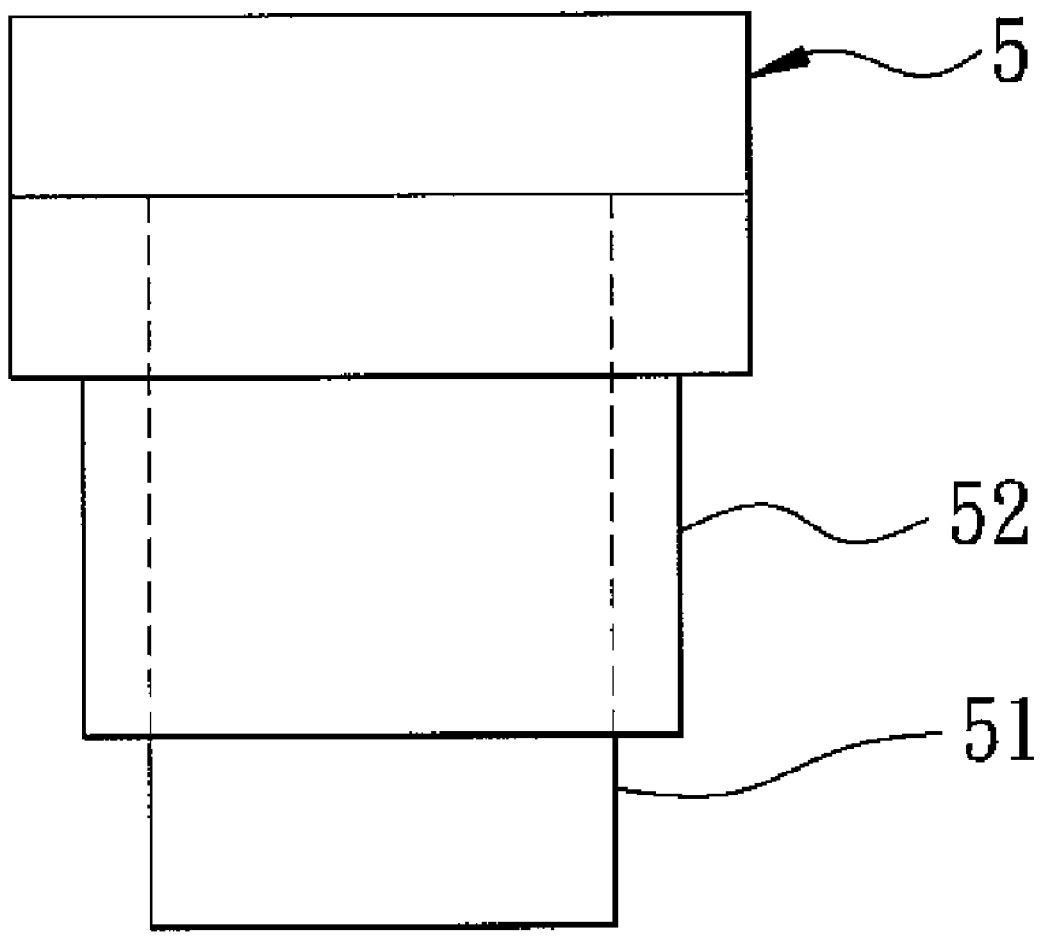
FIG. 13 shows a modified positioning member including a pin and a sleeved that is sleeved on the pin.

If each of the implant-position indicating units in the step 204 is configured as a pinhole formed in the plaster model of the machining data so that each of the implant-position indicating structures 33 is configured as a pinhole formed in the solid jaw model 3, with further reference to FIG. 13, each of the positioning members 5 will include a pin 51 and a sleeve 52 that is sleeved on the pin 51. When the pins 51 are removed from the negative template body 6 in the step 207, the sleeves 52 are embedded within the negative template body 6 (see FIG. 6) (i.e., disposed respectively within the implant guide holes 60).

Figure 14:
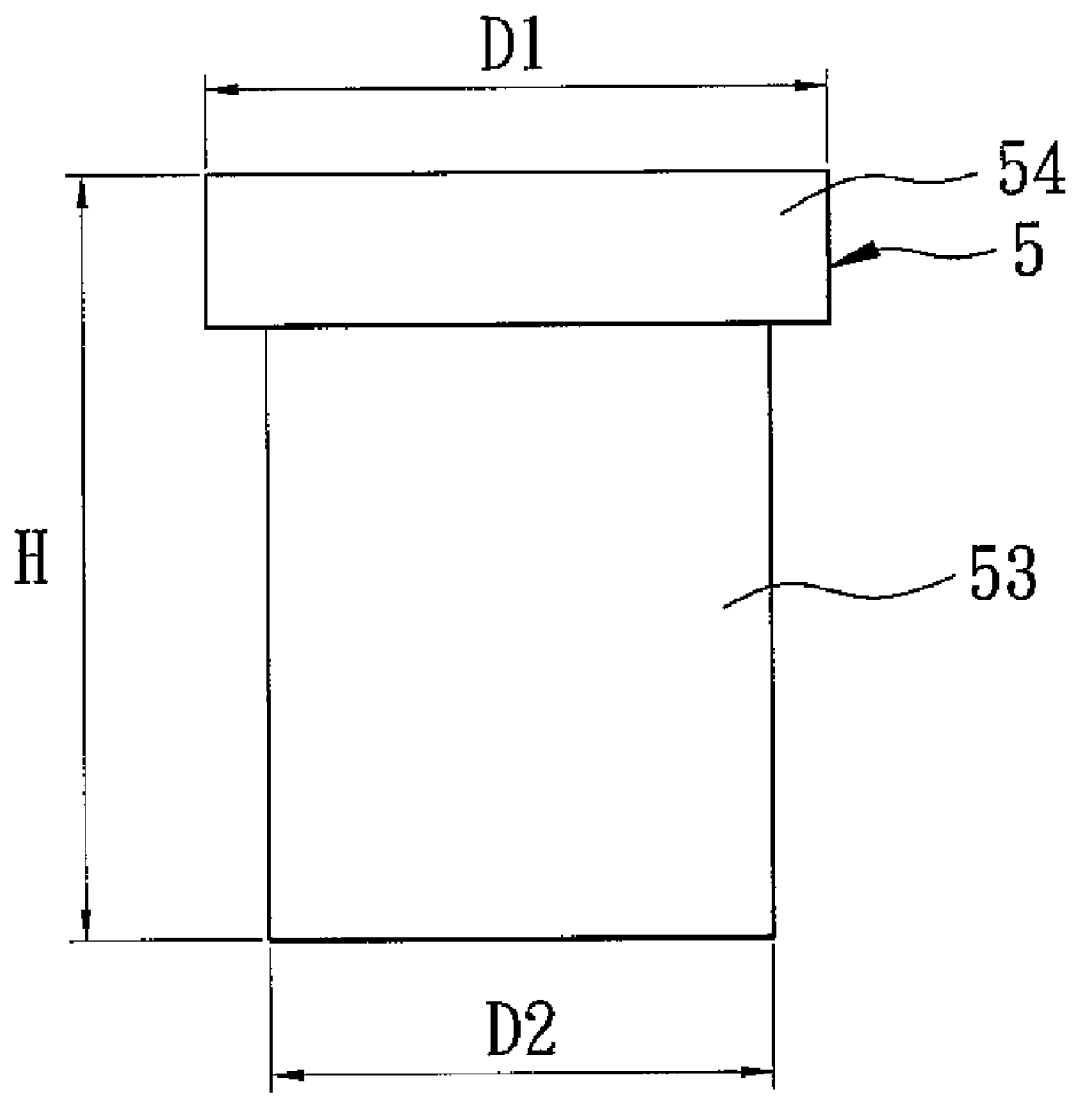
FIG. 14 shows another modified positioning member configured as a pin.
Figure 15:
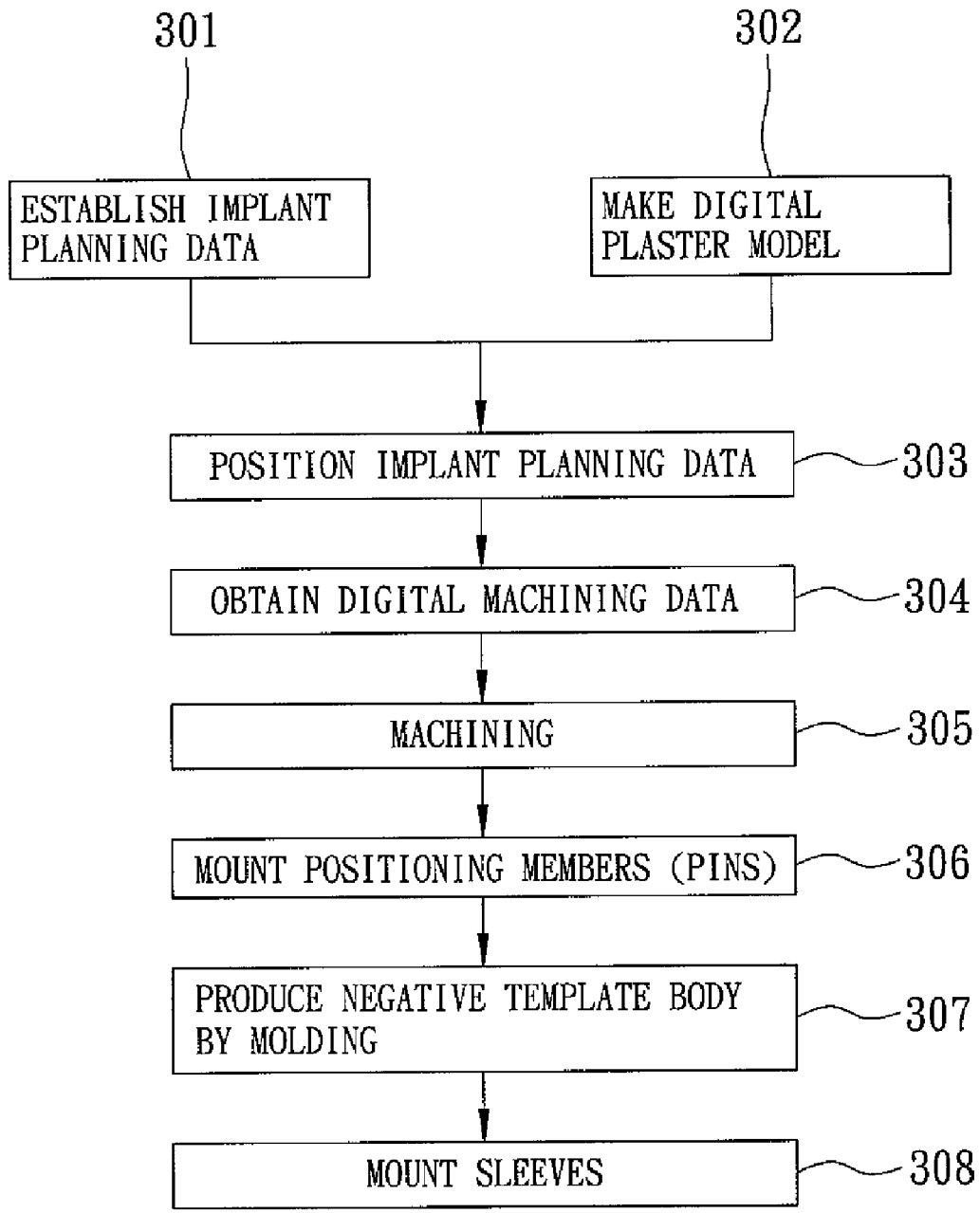
FIG. 15 is a flow chart of the second preferred embodiment of a method of making a surgical template used for dental implant surgery according to this invention.

FIG. 15 is a flow chart illustrating the second preferred embodiment of a method of making a surgical template used for dental implant surgery according to this invention, which is similar to the first preferred embodiment and which includes steps 301 to 308. The steps 301 to 308 are similar respectively to the steps 201 to 207 of the first preferred embodiment, respectively. Unlike the first preferred embodiment, in the step 302, each of the implant-position indicating units in the step 304 is configured as a pinhole formed in the plaster model of the machining data, and each of the implant-position indicating structures 33 in the step 305 is configured as a pinhole formed in the solid jaw model 3. In addition, with further reference to FIG. 14, each of the positioning members 5 in the step 306 is configured as a pin having a pin body 53 inserted into the corresponding pinhole in the solid jaw model 3, and a head 54 exposed outwardly of the corresponding pinhole in the solid jaw model 3 and spaced apart from the pinhole in the solid jaw model 3 by a predetermined distance. In the step 308, with reference to FIGS. 11 and 12, a plurality of sleeves 8 are inserted respectively into the implant guide holes 60 in the negative template body 6 (see FIG. 6). Each of the sleeves 8 has a sleeve body 82 and a flange 81 extending radially and outwardly from an end of the sleeve body 82, and abuts against an outer surface of the negative template body 6 (see FIG. 6).

The flanges 81 have an outer diameter (D1) the same as that of the heads 54. The sleeve bodies 82 have an outer diameter (D2) the same as that of the pins 53. The outer diameters (D1, D2) are set according to the implant system used by the dentist. Each of the positioning members 5 has a length (H) that is determined by the length required for the solid jaw model 3 and the implant depth of the implant planning data.

Figure 16:
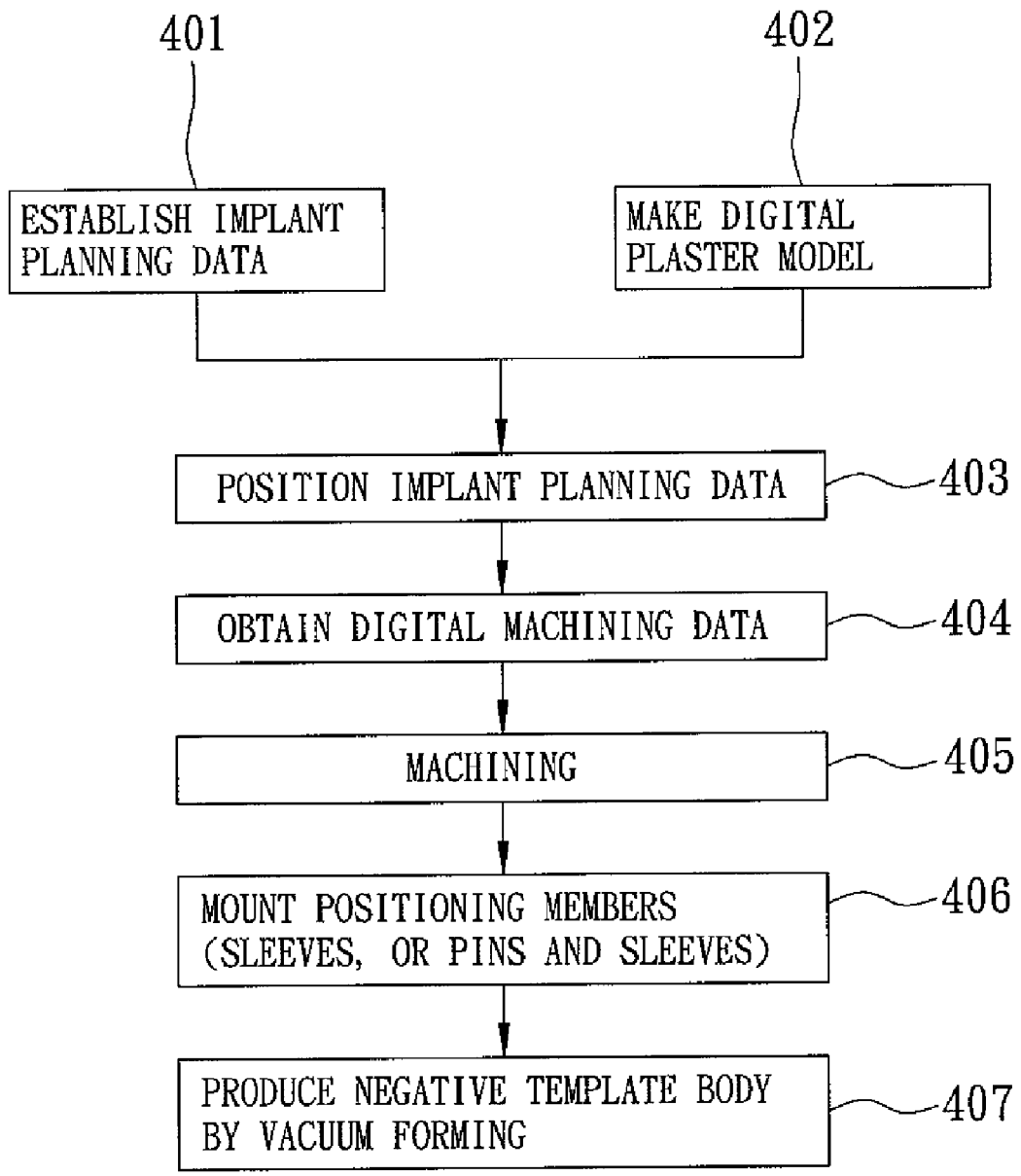
FIG. 16 is a flow chart of the third preferred embodiment of a method of making a surgical template used for dental implant surgery according to this invention.

FIG. 16 is a flow chart illustrating the third preferred embodiment of a method of making a surgical template used for dental implant surgery according to this invention, which is similar to the first preferred embodiment and which includes steps 401 to 407. The steps 401 to 406 are the same as the steps 201 to 206 of the first preferred embodiment, respectively. The step 407 is the different from the step 207 of the first preferred embodiment in that the negative template body 6 (see FIG. 6) is produced by a vacuum forming process instead of a molding process.

The vacuum forming process includes the following steps:
(1) A plastic sheet (not shown) made of the dental material is prepared.
(2) The plastic sheet is heated and softened.
(3) The softened plastic sheet is placed on the solid jaw model 3 and the positioning members 5. Each of the positioning members 5 is configured as a sleeve, or includes a pin 51 and a sleeve 52.
(4) A vacuum is applied to the softened plastic sheet to allow the softened plastic sheet to deform such that a side surface of the softened plastic sheet is complementary in structure to an assembly of the solid jaw model 3 and the positioning members 5.
(5) The deformed plastic sheet is hardened.
(6) The hardened plastic sheet is trimmed.
(7) In case that each of the positioning members 5 is configured as the sleeve, the solid jaw model 3 is removed from the trimmed plastic sheet. In case that each of the positioning members 5 includes the pin 51 and the sleeve 52, the pins and the solid jaw model 3 are removed from the trimmed plastic sheet.
(8) The trimmed plastic sheet is ground and polished.

Figure 17:
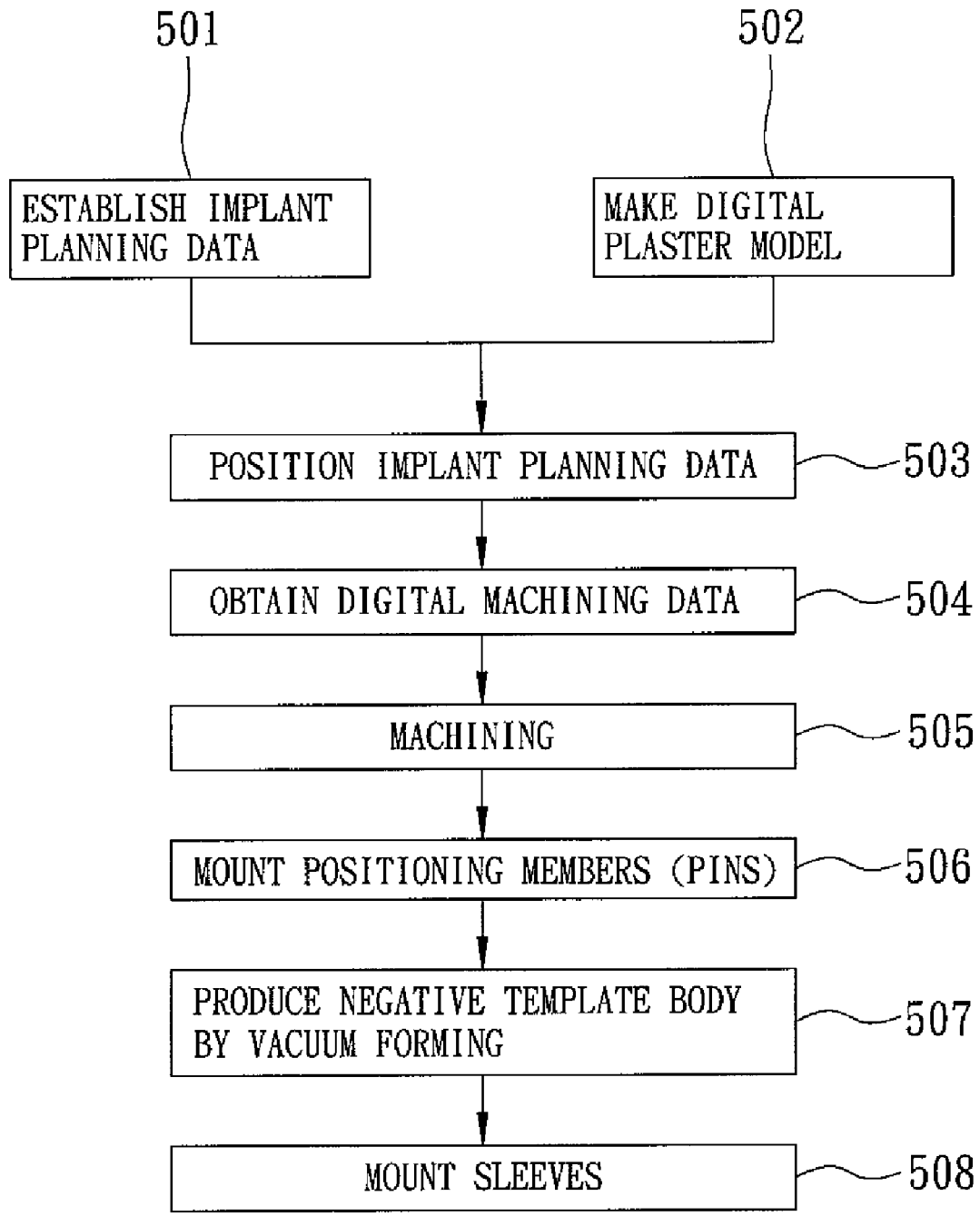
FIG. 17 is a flow chart of the fourth preferred embodiment of a method of making a surgical template used for dental implant surgery according to this invention.

FIG. 17 is a flow chart illustrating the fourth preferred embodiment of a method of making a surgical template used for dental implant surgery according to this invention, which is similar to the second preferred embodiment and which includes steps 501 to 508. The steps 501 to 506 are the same as the steps 301 to 306 of the second preferred embodiment, respectively. The step 507 is the different from the step 307 of the second preferred embodiment in that the negative template body 6 (see FIG. 6) is produced by a vacuum forming process. The step 508 is the same as the step 308 of the second preferred embodiment.

Figure 18:
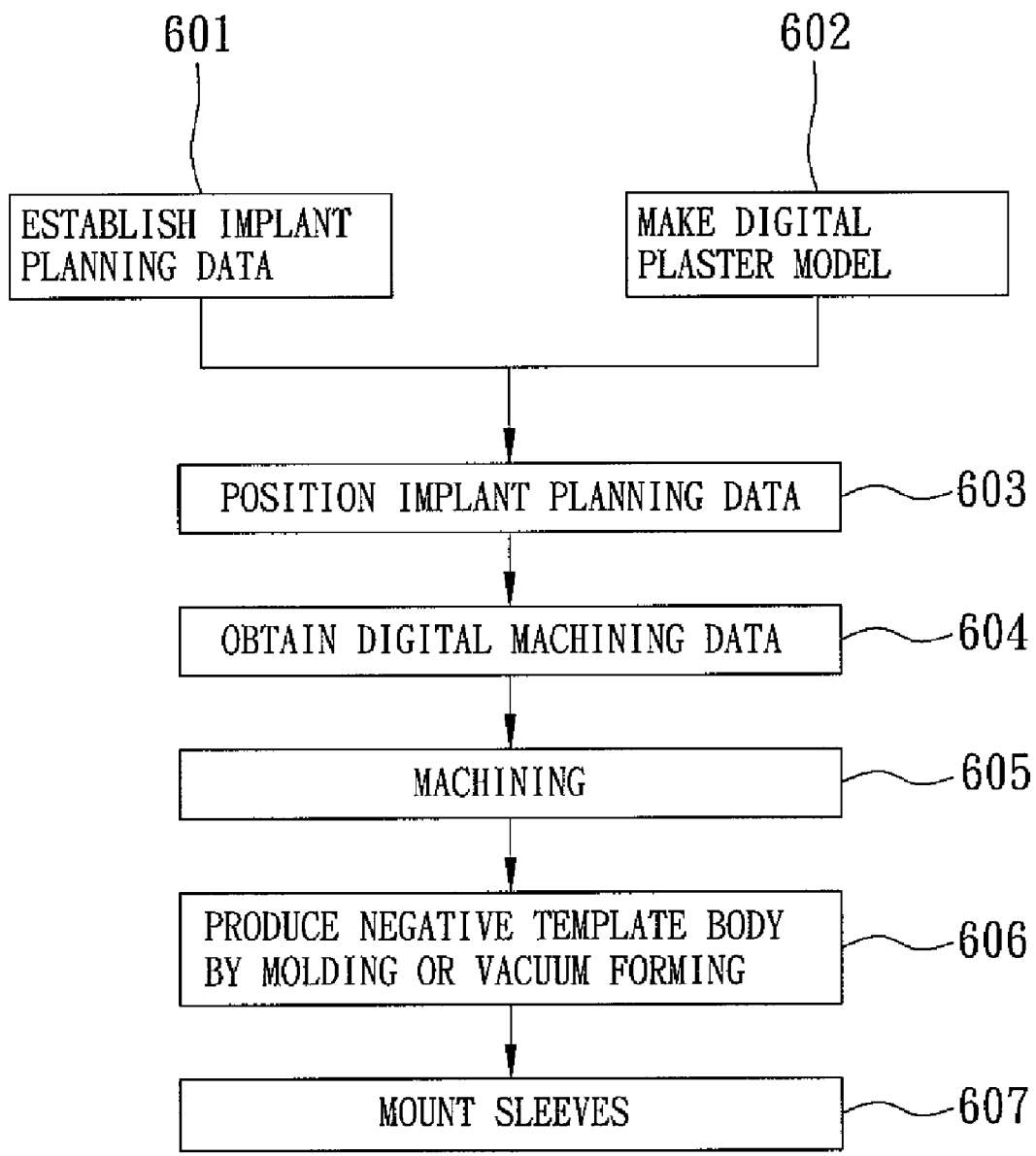
FIG. 18 is a flow chart of the fifth preferred embodiment of a method of making a surgical template used for dental implant surgery according to this invention.

FIG. 18 is a flow chart illustrating the fifth preferred embodiment of a method of making a surgical template used for dental implant surgery according to this invention, which is similar to the first preferred embodiment and which includes steps 601 to 607. The steps 601 to 603 are the same as the steps 201 to 203 of the first preferred embodiment, respectively. In the step 604, each of the implant-position indicating units is configured as a pin extending from the plaster model of the machining data. In the step 605, each of the implant-position indicating structures 33 is configured as a pin extending from the solid jaw model 3. This embodiment is different from the previous embodiments in that mounting of the positioning members 5 is omitted. The step 607 is different from the step 207 of the first preferred embodiment in that the negative template body 6 (see FIG. 6) is produced by a vacuum forming process to form a plurality of implant guide holes 60 (see FIG. 11). In the step 607, a plurality of sleeves 8 are inserted respectively into the implant guide holes 60 in the negative template body 6.

In view of the above, the method of this invention has the following advantages:

1. Referring to FIG. 6, since the digital plaster model (III) is a positive model, the implant planning data can be applied accurately, precisely, and efficiently to the digital plaster model (III), thereby allowing the implant guide holes 60 to be formed at ideal positions. That is, time required for correcting the distortions in CT scan of the patient's jaw can be reduced significantly, thereby promoting the efficiency of the method of this invention and reducing the manufacturing costs of the surgical template.
2. The sizes of the pins 5, 51 and the sleeves 8, 52 can be changed according to selected depths and lengths of the implants, thereby improving the implant-guiding effect and application flexibility of the surgical template.

With this invention thus explained, it is apparent that numerous modifications and variations can be made without departing from the scope and spirit of this invention. It is therefore intended that this invention be limited only as indicated by the appended claims.

We claim:

1. A method of making a surgical template used for a computer-guided dental implant surgery, comprising the steps of:
   (a) producing a three-dimensional model by a CT scanning performed on a patient's jaw and establishing corresponding implant planning data to obtain a digital model of an assembly of the patient's jaw and the implant planning data;
   (b) making a negative model by direct impression modeling of the patient's jaw, and then a positive plaster model from the negative model, and producing a digital plaster model corresponding to the positive plaster model;
   (c) positioning the digital model of the assembly of the patient's jaw and the implant planning data relative to the digital plaster model to allow the digital plaster model to have the implant planning data;
   (d) integrating the digital plaster model with the implant planning data to obtain a digital machining data;
   (e) holding and machining a modeling block at a machining position by a machine according to the digital machining data to form a solid jaw model corresponding to the patient's jaw and having teeth, gums, and at least one implant-position indicating structure;
   (f) mounting a positioning member at the implant-position indicating structure; and
   (g) producing a negative template body from an assembly of the solid jaw model and the positioning member with a thermoplastic dental material by one of a molding process and a vacuum forming process such that the negative template body has a lower surface complementary to the assembly of the solid jaw model and the positioning member, and at least one implant guide hole formed therethrough at a position corresponding to the implant-position indicating structure; whereby, the surgical template includes the negative template body.

2. The method as claimed in claim 1, wherein, in said step (e), the machine is a five-axis CNC machine.

3. The method as claimed in claim 1, wherein, in said step (e), the modeling block is made of one of plaster and a wood substitute material.

4. The method as claimed in claim 1, wherein, in said step (d), the digital machining data includes a plaster model and at least one implant-position indicating unit.

5. The method as claimed in claim 4, wherein, in said step (d), the implant-position indicating unit is configured as one of a pinhole formed in the plaster model of the machining data, and a pin extending from the plaster model of the machining data.

6. The method as claimed in claim 5, wherein, in said step (g), the negative template body is produced by the molding process, the molding process including the substeps of:
   (1) coating the assembly of the solid jaw model and the positioning member with a thermoplastic first coating material such that an outer surface of the first coating material is aligned with an end surface of the positioning member;
   (2) coating the first coating material with a second coating material having a melting point higher than that of the first coating material;
   (3) heating the first and second coating materials to a temperature between the melting points of said first and second coating materials so as to melt only the first coating material, thereby forming a mold cavity such that the solid jaw model, the positioning member, and the second coating material constitute cooperatively a mold;
   (4) heating and pouring the dental material into the mold cavity;
   (5) allowing the dental material to cure to thereby form the negative template body; and
   (6) removing the second coating material and the solid jaw model from the negative template body.

7. The method as claimed in claim 6, wherein, in said step (g), said molding process further includes a substep (7) of, after said substep (6), grinding and polishing the negative template body.

8. The method as claimed in claim 6, wherein:
   in said step (d), the implant-position indicating unit is configured as the pin extending from the plaster model of the machining data so that, in said step (e), the implant-position indicating structure is configured as a pin extending from the solid jaw model; and
   in said step (f), the positioning member is configured as a sleeve that is sleeved on the pin extending from the solid jaw model so that, in said step (g), when the negative template body is formed, the sleeve is embedded within the negative template body; whereby, the surgical template further includes the sleeve.

9. The method as claimed in claim 5, wherein, in said step (g), the negative template body is produced by the molding process, the molding process including the substeps of:
   (1) coating the assembly of the solid jaw model and the positioning member with a thermoplastic first coating material such that an outer surface of the first coating material is aligned with an end surface of the positioning member;
   (2) coating the first coating material with a second coating material having a melting point higher than that of the first coating material;
   (3) heating the first and second coating materials to a temperature between the melting points of said first and second coating materials so as to melt only the first coating material, thereby forming a mold cavity such that the solid jaw model, the positioning member, and the second coating material constitute cooperatively a mold;
   (4) heating and pouring the dental material into the mold cavity;
   (5) allowing the dental material to cure to thereby form the negative template body; and (6) removing the second coating material, said positioning member, and the solid jaw model from the negative template body.

10. The method as claimed in claim 9, wherein, in said step (g), said molding process further includes a substep (7) of, after said substep (6), grinding and polishing the negative template body.

11. The method as claimed in claim 9, wherein:
in said step (d), the implant-position indicating unit is configured as the pinhole formed in the plaster model of the machining data so that, in said step (e), the implant-position indicating structure is configured as a pinhole formed in the solid jaw model; and
in said step (f), the positioning member is configured as a pin having a pin body inserted into the pinhole in the solid jaw model, and a head exposed outwardly of the pinhole in the solid jaw model and spaced apart from the pinhole in the solid jaw model by a predetermined distance so that, in said step (g), when the negative template body is formed, and when the positioning member is removed from the negative template body, an implant guide hole is formed in the negative template body.

12. The method as claimed in claim 11, after said step (g), further comprising a step (h) of inserting a sleeve into the implant guide hole in the negative plate body, the sleeve having a sleeve body disposed within the implant guide hole, and a flange extending radially and outwardly from an end of the sleeve body and abutting against an outer surface of the negative template body; whereby, the surgical template further includes the sleeve.

13. The method as claimed in claim 6, wherein:
in said step (d), the implant-position indicating unit is configured as the pinhole formed in the plaster model of the machining data so that, in said step (e), the implant-position indicating structure is configured as a pinhole formed in the solid jaw model;
in said step (f), a portion of the positioning member is inserted into the pinhole formed in the solid jaw model, and includes a pin constituting the portion of the positioning member, and a sleeve that is sleeved on the pin; and
in said substep (6) of said step (g), when the second coating material and the pin are removed from the negative template body, the sleeve is embedded within the dental material;
whereby, the surgical template further includes the sleeve.

14. The method as claimed in claim 5, wherein, in said step (g), the negative template body is produced by the vacuum forming process, the vacuum forming process including the substeps of:
(1) preparing a plastic sheet made of the dental material;
(2) heating and softening the plastic sheet;
(3) placing the softened plastic sheet on the solid jaw model and the positioning member;
(4) applying a vacuum to the softened plastic sheet to allow the softened plastic sheet to deform so that a side surface of the softened plastic sheet is complementary in structure to an assembly of the solid jaw model and the positioning member;
(5) hardening the deformed plastic sheet;
(6) trimming the hardened plastic sheet; and
(7) removing the solid jaw model and the positioning member from the trimmed plastic sheet.

15. The method as claimed in claim 14, wherein, in said step (g), the vacuum forming process further includes a step (8) of, after said substep (7), grinding and polishing the trimmed plastic sheet.

16. The method as claimed in claim 14, wherein:
in said step (d), the implant-position indicating unit is configured as the pin extending from the plaster model of the machining data so that, in said step (e), the implant-position indicating structure is configured as a pin extending from the solid jaw model; and
in said step (f), the positioning member is configured as a sleeve that is sleeved on the pin extending from the solid jaw model so that, in said step (g), when the negative template body is formed, the sleeve is embedded within the negative template body; whereby, the surgical template further includes the sleeve.

17. The method as claimed in claim 14, wherein:
in said step (d), the implant-position indicating unit is configured as the pinhole formed in the plaster model of the machining data so that, in said step (e), the implant-position indicating structure is configured as a pinhole formed in the solid jaw model; and
in said step (f), the positioning member is configured as a pin having a pin body inserted into the pinhole in the solid jaw model, and a head exposed outwardly of the pinhole in the solid jaw model and spaced apart from the pinhole in the solid jaw model by a predetermined distance so that, in said step (g), when the negative template body is formed, and when the positioning member is removed from the negative template body, an implant guide hole is formed in the negative template body.

18. The method as claimed in claim 14, after said step (g), further comprising a step (h) of inserting a sleeve into the implant guide hole in the negative plate body, the sleeve having a sleeve body disposed within the implant guide hole, and a flange extending radially and outwardly from an end of the sleeve body and abutting against an outer surface of the negative template body; whereby, the surgical template further includes the sleeve.

19. The method as claimed in claim 14, wherein:
in said step (d), the implant-position indicating unit is configured as the pinhole formed in the plaster model of the machining data so that, in said step (e), the implant-position indicating structure is configured as a pinhole formed in the solid jaw model;
in said step (f), the positioning member is inserted into the pinhole formed in the solid jaw model, and is configured as a pin and a sleeve that is sleeved on the pin; and
in said substep (7) of said step (g), after the solid jaw model and the positioning member are removed from the trimmed plastic sheet, the sleeve is embedded within the plastic sheet.

20. A method of making a surgical template used for a computer-guided dental implant surgery, comprising the steps of:
(a) producing a three-dimensional model by a CT scanning performed on a patient's jaw and establishing corresponding implant planning data to obtain a digital model of an assembly of the patient's jaw and the implant planning data;
(b) making a negative model by direct impression modeling of the patient's jaw, and then a positive plaster model from the negative model, and producing a digital plaster model corresponding to the positive plaster model;
(c) positioning the digital model of the assembly of the patient's jaw and the implant planning data relative to the digital plaster model to allow the digital plaster model to have the implant planning data;
(d) integrating the digital plaster model with the implant planning data to obtain a digital machining data, the digital machining data including a plaster model and at least one implant-position indicating unit configured as a pin extending from the plaster model;

(e) holding and machining a modeling block at a machining position by a machine according to the digital machining data to form a solid jaw model corresponding to the patient's jaw and having teeth, gums, and at least one implant-position indicating structure configured as a pin extending from the solid jaw model; and (f) producing a negative template body from the solid jaw model with a thermoplastic dental material by one of a molding process and a vacuum forming process such that the negative template body has a lower surface complementary to the solid jaw model, and at least one implant guide hole formed therethrough at a position corresponding to the implant-position indicating structure; whereby, the surgical template includes the negative template body.

21. The method as claimed in claim 20, after said step (e), further comprising a step (g) of inserting a sleeve into the implant guide hole in the negative template body, the sleeve having a sleeve body disposed within the implant guide hole, and a flange extending radially and outwardly from an end of the sleeve body and abutting against an outer surface of the negative template body; whereby, the surgical template further includes the sleeve.

22. The method as claimed in claim 20, wherein, in said step (e), the modeling block is made of one of plaster and a wood substitute material.

* * * * *